(12) United States Patent
Inoue et al.

(10) Patent No.: US 8,779,372 B2
(45) Date of Patent: Jul. 15, 2014

(54) RADIATION IMAGE PICKUP APPARATUS, RADIATION IMAGE PICKUP SYSTEM, AND METHOD FOR MANUFACTURING RADIATION IMAGE PICKUP APPARATUS

(75) Inventors: Masato Inoue, Kumagaya (JP); Masayoshi Akiyama, Yokohama (JP); Shinichi Takeda, Honjo (JP); Satoru Sawada, Kodama-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 280 days.

(21) Appl. No.: 13/161,709

(22) Filed: Jun. 16, 2011

(65) Prior Publication Data

US 2011/0315887 A1  Dec. 29, 2011

(30) Foreign Application Priority Data

Jun. 23, 2010 (JP) ................. 2010-142951

(51) Int. Cl.
*G01T 1/20* (2006.01)
*G01T 1/24* (2006.01)

(52) U.S. Cl.
USPC ............. 250/370.11; 250/361 R; 250/370.09

(58) Field of Classification Search
USPC .................... 250/361 R, 369, 370.09–370.11
See application file for complete search history.

(56) References Cited

U.S. PATENT DOCUMENTS

| 6,121,620 | A | * | 9/2000 | Tashiro et al. | ............ 250/370.11 |
| 2002/0038851 | A1 | * | 4/2002 | Kajiwara et al. | ............... 250/368 |
| 2010/0108893 | A1 | * | 5/2010 | Flitsch et al. | ............. 250/361 R |
| 2010/0243908 | A1 | * | 9/2010 | Shoji et al. | ............... 250/370.11 |

FOREIGN PATENT DOCUMENTS

| JP | 2005172511 A | 6/2005 |
| JP | 2006039390 A | 2/2006 |
| JP | 2008277454 A | 11/2008 |
| JP | 2010087080 A | 4/2010 |
| WO | 2008142135 A1 | 11/2008 |

* cited by examiner

*Primary Examiner* — Casey Bryant
(74) *Attorney, Agent, or Firm* — Canon U.S.A., Inc., IP Division

(57) ABSTRACT

A radiation image pickup apparatus includes a base which transmits ultraviolet rays, a plurality of image pickup elements, a scintillator, at least one ultraviolet peelable adhesive arranged between the base and the image pickup elements so as to fix the base and the image pickup elements in a predetermined position with respect to each other, and a heat peelable adhesive arranged between the image pickup elements and the scintillators so as to fix the image pickup elements to the scintillator.

20 Claims, 8 Drawing Sheets

RADIATION IMAGE PICKUP APPARATUS, RADIATION IMAGE PICKUP SYSTEM, AND METHOD FOR MANUFACTURING RADIATION IMAGE PICKUP APPARATUS

BACKGROUND OF THE INVENTION

1. Field of the Invention

The present invention relates to a radiation image pickup apparatus detecting radiation rays, a radiation image pickup system, and a method for manufacturing a radiation image pickup apparatus, and more particularly relates to a radiation image pickup apparatus used for a medical image diagnosis apparatus, a nondestructive inspection apparatus, an analysis apparatus, and the like.

2. Description of the Related Art

A commercially available single crystal semiconductor wafer is generally smaller in size than a glass substrate. Hence, in order to form a large-area detector using a single crystal semiconductor wafer, a single crystal semiconductor wafer in which detection elements are formed is divided to form a plurality of image pickup element chips, and an appropriate number of the image pickup element chips are arranged to form a detector having a desired area. Typically, the image pickup element chips are permanently fixed to a based board to form the detector. One example of this technique is described in U.S. Pat. No. 6,800,857 (also published as U.S. Patent Application Publication No. 2002/0038851), which is assigned to Canon Kabushiki Kaisha the assignee of the present application. U.S. Pat. No. 6,800,857 discloses that in order to reduce cost, before image pickup element chips are adhered to the base board which functions as a part of an apparatus, the image pickup element chips are inspected, and an image pickup element chip which is detected as a defective element, if any, is exchanged. In addition, it has also been disclosed that after the inspection and the exchange are performed, the image pickup element chips are fixed to the base board by adhesion.

However, with the technique disclosed in U.S. Pat. No. 6,800,857, after a plurality of image pickup element chips is adhered to the base board, it is difficult to exchange one or more defective image pickup element chips which are discovered by inspection or testing. For example, when a defective image pickup element chip is peeled off, an image pickup element chip having no defect may be fractured by an external stress applied thereto in some cases. In addition, even if an image pickup element chip were to be replaced after assembly, properties of an image pickup element chip having no defect may be degraded in some cases by a solvent used for dissolving an adhesive.

SUMMARY OF THE INVENTION

The present invention is made in consideration of the problems described above and provides a radiation image pickup apparatus in which one or more image pickup elements can be easily exchanged.

One aspect of the present invention is directed to a radiation image pickup apparatus which comprises: a base which transmits ultraviolet rays; a plurality of image pickup elements each including a plurality of pixels, each pixel includes a sensor portion for converting light into an image signal; a scintillator arranged on the image pickup elements at a side opposite to the base; at least one ultraviolet peelable adhesive which is arranged between the base and the image pickup elements so as to fix the base and the image pickup elements in a predetermined position with respect to each other; and a heat peelable adhesive which is arranged between the image pickup elements and the scintillator and which fixes the image pickup elements to the scintillator.

According to the present invention, a radiation image pickup apparatus in which one or more image pickup elements are easily exchanged can be obtained.

Further features of the present invention will become apparent from the following description of exemplary embodiments with reference to the attached drawings.

DESCRIPTION OF THE EMBODIMENTS

Hereinafter, embodiments of a radiation image pickup apparatus, a radiation image pickup system, and a method for manufacturing a radiation image pickup apparatus, according to the present invention, will be described with reference to the drawings. In the present invention, light includes visible light and infrared light, and radiation rays include X-rays, α rays, β rays, and γ rays.

Embodiment 1

Figure 1A:
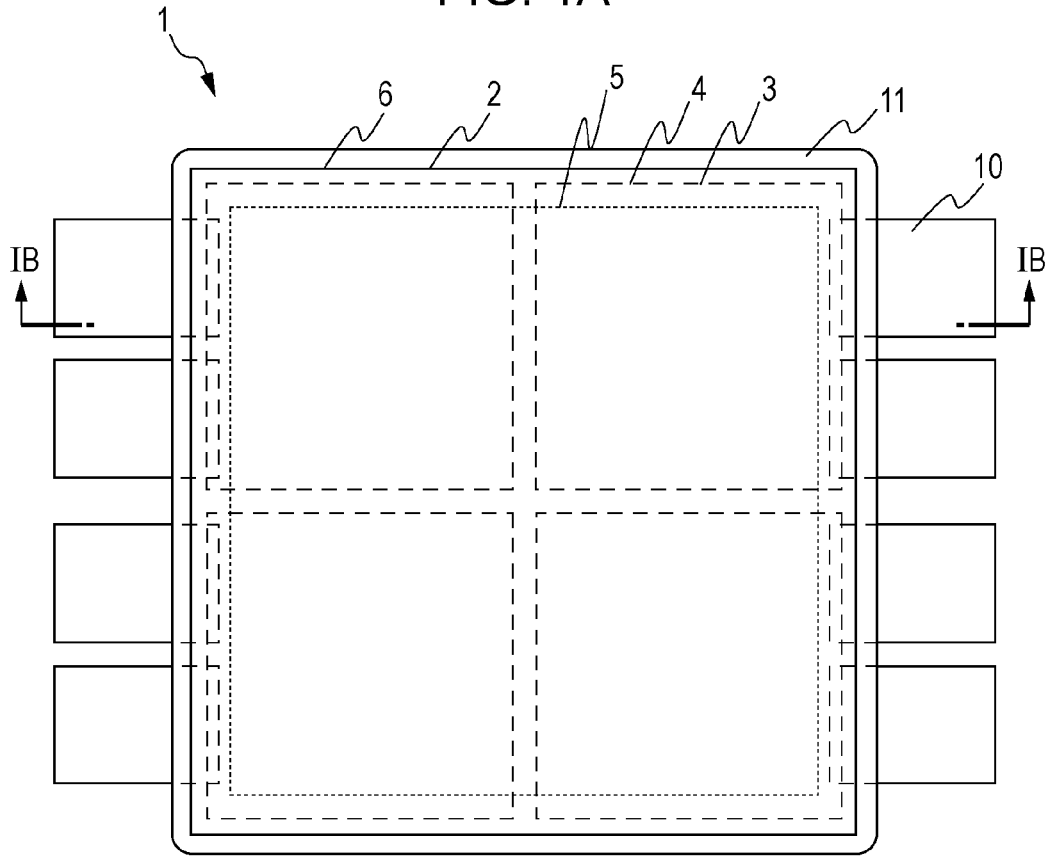
FIGS. 1A and 1B are a plan view and a cross-sectional view, respectively, of a radiation image pickup apparatus according to Embodiment 1.
Figure 1B:
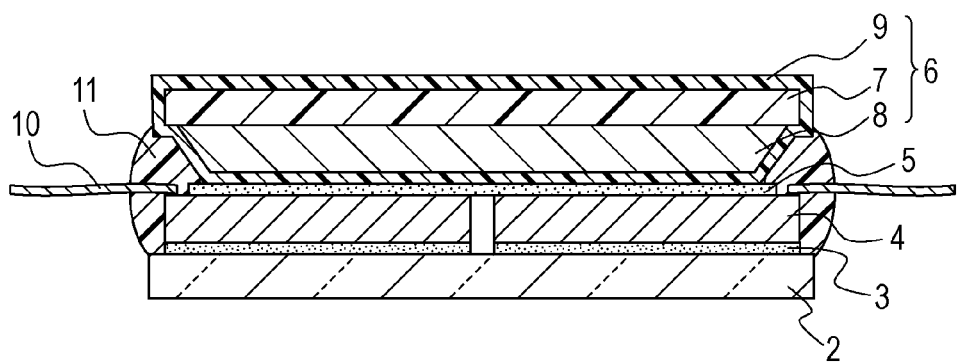

FIGS. 1A and 1B each shows a different view of a radiation image pickup apparatus according to a first embodiment. FIG. 1A is a plan view of the radiation image pickup apparatus, and FIG. 1B is a cross-sectional view of the radiation image pickup apparatus taken along the line IB-IB of FIG. 1A.

As shown in FIGS. 1A and 1B, a radiation image pickup apparatus 1 includes a base 2, a plurality (four in this case) of image pickup elements 4 arranged (fixed) on the base 2 with ultraviolet peelable adhesives 3 provided therebetween, and a scintillator 6 arranged over (fixed on) the image pickup elements 4 with a heat peelable adhesive 5 provided therebetween. A wiring board 10 for transferring a signal (image signal) between the image pickup elements 4 and an external circuit (not shown) is connected to each of the image pickup elements 4. In order to reduce electrical and mechanical influences generated when the image pickup elements 4 come into contact with each other, the image pickup elements 4 are arranged on the base 2 with a separating space provided therebetween. It should be noted that the number of the image pickup elements 4 fixed on the base 2 is not limited to four; indeed, only one or more image pickup elements 4 may be arranged in the manner illustrated by FIGS. 1A and 1B.

Each of the image pickup elements 4 has a plurality of pixels; and, in turn, each pixel includes a switching element and a sensor portion. The sensor portion serves to detect visible light emitted from the scintillator, and to convert the visible light into a signal (image signal) indicative of the amount of light incident thereupon. An image pickup element 4 may be implemented as any one of a complementary metal-oxide semiconductor (CMOS) sensor, a charge coupled device (CCD) sensor, an amorphous silicon (a-Si) sensor having a pixel formed of a TFT, and a metal-insulator-semiconductor (MIS) sensor or a PIN sensor using amorphous silicon, and an SOI (silicon on insulator) sensor. Although a flexible printed-circuit board (FPC) is suitably used for the wiring board 10, a rigid wiring board may also be used.

The scintillator 6 includes a substrate 7, scintillator layer 8, and a protective layer 9. The scintillator layer 8 converts radiation rays, such as X-rays, into light which can be sensed by the image pickup element 4. For the substrate 7, amorphous carbon (a-C), aluminum, a resin, or the like may be used. For the scintillator layer 8, a columnar crystal, such as CsI:Tl, or a particulate crystal, such as GOS, which converts radiation rays, such as X-rays, into light may be used.

In order to protect the scintillator layer 8 from moisture and/or impact or pressure from the outside, the protective layer 9 is formed from a polyparaxylylene, a hot melt resin, or the like. Although a glass, which is an ultraviolet transmitting material, is used for the base 2, any material having a high transmittance of ultraviolet rays may be used. For example, quartz, a resin such as an acrylic resin, and ceramic may also be used for the base 2. In the first embodiment, the ultraviolet rays are defined as a light having a wavelength of approximately 400 nm or less. In order to shorten the irradiation time, the transmittance of ultraviolet rays is preferably 60% or more. The periphery of the radiation image pickup apparatus 1 is fixed between the base 2 and the scintillator 6 with a resin 11 so as to suppress the entry of moisture, dust and the like from the outside; and the image pickup elements 4 are sealed inside. The wring board 10 is arranged to penetrate the resin 11. For the resin 11, an acrylic resin, an epoxy resin, a silicone resin, or the like is used, and a black resin which absorbs light is preferable. The reason for this is that when the base 2 transmits light having a wavelength to be sensed by the image pickup element 4, light from a light emitting element of a different circuit board is prevented from entering the image pickup element 4 as stray light, and the image quality is suppressed from being degraded.

The ultraviolet peelable adhesive 3 is arranged in order to fix the base 2 and the image pickup element 4 in a predetermined position with respect to each other. As illustrated in FIGS. 1A and 1B, it is important that the ultraviolet peelable adhesive 3 fixes the position of the base 2 and the image pickup element 4 such that a predetermined space exists between adjacent image pickup elements 4, and to enable the image pickup element 4 to be easily exchanged in the case of repair. To that end, the ultraviolet peelable adhesive 3 should preferably fix the position of the base 2 and the image pickup element 4 quickly, as well as allow for easy detachment thereof in case of repair. Thus, in order to shorten the irradiation time for effective fixing, the transmittance of ultraviolet rays through the ultraviolet peelable adhesive 3 is preferably 60% or more.

The heat peelable adhesive 5 is arranged in order to fix the image pickup elements 4 to the scintillator 6 and to enable the image pickup elements 4 or the scintillator 6 to be easily exchanged in case of necessary repair. The ultraviolet peelable adhesive 3 is an ultraviolet reaction type adhesive and reacts with incident ultraviolet rays to decrease its adhesive strength. The heat peelable adhesive 5 is a heat reaction type adhesive and reacts with heat at a predetermined temperature or more to decrease its adhesive strength. That is, since there are two different types of methods each decreasing the adhesive strength, an object to be peeled off can be selected by using one of the different types of methods. In the case in which the adhesive strengths are decreased by the same method under the same conditions, for example, when the scintillator 6 is removed, after lifted up therewith, one or more image pickup elements may fall down or may come into contact with another image pickup element in some cases. The probability in which an image pickup element having no defect is broken as described above can be reduced.

Figure 2A:
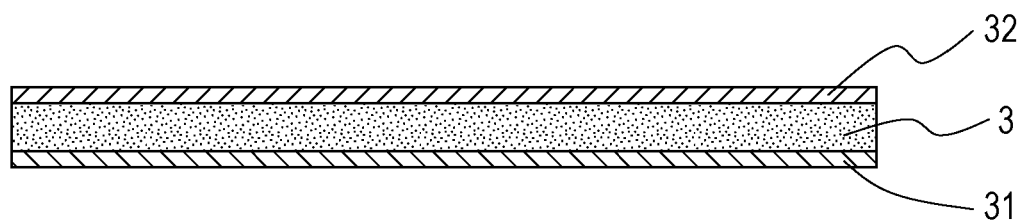
FIGS. 2A and 2B are cross-sectional views each showing a sheet of a reaction-induced phase separation material provided with separators.
Figure 2B:
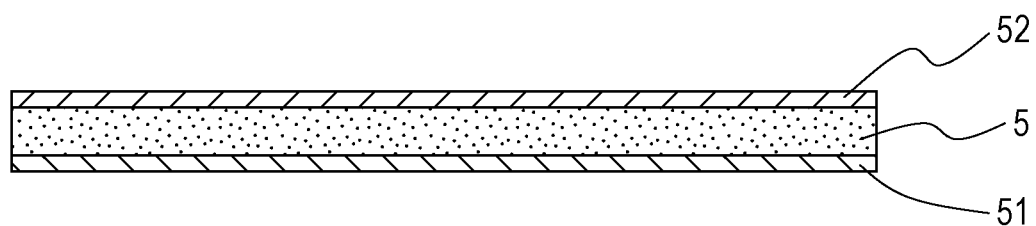

FIGS. 2A and 2B are each a cross-sectional view of a sheet in which a peelable adhesive which can be easily peeled off is provided with separators. FIG. 2A shows a sheet in which separators 31 and 32 are arranged on two surfaces of the ultraviolet peelable adhesive 3. FIG. 2B shows a sheet in which separators 51 and 52 are arranged on two opposite surfaces of the heat peelable adhesive 5.

A material performing a curing reaction by ultraviolet rays as the ultraviolet peelable adhesive 3 has a radiation-polymerizable functional group which is derived from a polyfunctional monomer or oligomer and which is bonded to a side chain or a main chain of a removable adhesive polymer.

As a polymer functioning as a main chain, there may be used an acrylic polymer selected from a homopolymer and a copolymer, each containing an acrylic acid ester as a primary constituent monomer unit, a copolymer formed with another functional monomer, or a mixture of these polymers mentioned above. For example, an acrylic ester of an alkyl alcohol having 1 to 10 carbon atoms, a methacrylic acid ester, vinyl acetate, acrylonitrile, or vinyl ethyl ether may be preferably used.

In addition, the above acrylic polymer may be used alone, or at least two types thereof may be used in combination. As the polyfunctional monomer or oligomer which is introduced into a side chain or a main chain of an acrylic polymer and which forms a radiation-polymerizable functional group, there may be widely used a low molecular weight compound which has at least two photopolymerizable carbon-carbon double bonds in a molecule and which is able to form a three-dimensional network by light irradiation. In particular, for example, there may be mentioned pentaerythritol diacrylate, pentaerythritol triacrylate, pentaerythritol dimethacrylate, pentaerythritol trimethacrylate, dipentaerythritol diacrylate, dipentaerythritol triacrylate, dipentaerythritol tetraacrylate, dipentaerythritol pentaacrylate, dipentaerythritol dimethacrylate, dipentaerythritol trimethacrylate, dipentaerythritol tetramethacrylate, dipentaerythritol pentamethacrylate, trimethylolpropane diacrylate, or trimethylolpropane dimethacrylate. In addition, the polyfunctional monomer or oligomer may be used alone, or at least two types thereof may be used in combination.

The heat peelable adhesive 5 uses a material which decreases its adhesive strength by heating and is formed, for example, of an adhesive mixed with heat-expandable microspheres containing a foaming agent.

Hereinafter, the adhesive mixed with heat-expandable microspheres containing a foaming agent will be described in detail.

As the adhesive, an appropriate adhesive, such as a rubber adhesive, an acrylic adhesive, a styrene-conjugated diene block copolymer adhesive, or a silicone adhesive, may be used, and an ultraviolet curable adhesive may also be used.

In addition, the adhesive may be blended, for example, with appropriate additives, such as a cross-linking agent, a tackifier, a plasticizer, a filler, and/or an antiaging agent, if needed.

In more particular, for example, there may be mentioned a rubber adhesive which uses at least one of natural rubbers and various types of synthetic rubbers as a base polymer and an acrylic adhesive which uses an acrylic polymer as a base polymer, the acrylic polymer including at least one component selected from an acrylic acid-based alkyl ester, such as an acrylic acid or a methacrylic acid, having an alkyl group of 20 carbon atoms or less, which generally indicates a methyl group, an ethyl group, a propyl group, a butyl group, a 2-ethylhexyl group, an isooctyl group, an isononyl group, an isodecyl group, a dodecyl, a lauryl group, a tridecyl group, a pentadecyl group, a hexadecyl group, a heptadecyl group, an octadecyl group, a nonadecyl group, an eicosyl group, or the like; an ester of acrylic acid or a methacrylic acid, having a functional group, such as a hydroxyethyl group, a hydroxypropyl group, or a glycidyl group; acrylic acid, methacrylic acid, itaconic acid, N-methylolacrylamide, acrylonitrile, methacrylonitrile, vinyl acetate, styrene, isoprene, butadiene, isobutylene, or vinyl ether.

The adhesive is properly selected in accordance with the purpose of use, such as the adhesive strength to an adherend, and an adhesive layer which is foamed and/or expanded by heating can be formed by blending a foaming agent with the adhesive.

As the foaming agent, various types of agents which achieve the above purpose may be used. Accordingly, for example, a foaming agent which is foamed and/or expanded at a higher temperature than an adhesion processing temperature of the adhesives may be used. As examples of the foaming agent which may be used, decomposition type inorganic foaming agents, such as ammonium carbonate, ammonium hydrogen carbonate, sodium hydrogen carbonate, ammonium nitrite, sodium borohydride, and azides may be used.

In addition, organic foaming agents, such as an azo compound, may also be used. As examples thereof, for example, there may be mentioned alkane fluorides, such as trichloromonofluoromethane and dichloromonofluoromethane; azo compounds, such as azobisisobutyronitrile, azodicarbonamide, and barium azodicarboxylate; hydrazine compounds, such as p-toluenesulfonyl hydrazide, diphenylsulfone-3,3'-disulfonyl hydrazide, 4,4'-oxybis(benzenesulfonyl hydrazide) and allylbis(sulfonyl hydrazide); semicarbazide compounds, such as ρ-toluoylenesulfonyl semicarbazide and 4,4'-oxybis(benzenesulfonyl semicarbazide); triazole compounds, such as 5-morphoryl-1,2,3,4-thiatriazole; N-nitroso compounds, such as N,N'-dinitrosopentamethylenetetramine and N,N'-dimethyl-N,N'-dinitrosoterephthalamide; and other low boiling-point compounds.

Furthermore, there may also be used heat-expandable microspheres in which an appropriate substance, such as isobutane, propane, or pentane, which easily gasifies and has a thermal expansion property, is enclosed in a shell-forming material by a coacervation method, an interfacial polymerization method, or the like. Heat-expandable microspheres having an average particle diameter of 1 to 50 μm are used. However, heat-expandable microspheres having an average diameter smaller than that described above may also be used.

In addition, as the shell-forming material forming the heat-expandable microspheres, for example, the following materials may be mentioned. For example, there may be mentioned a vinylidene chloride-acrylonitrile copolymer, a poly (vinyl alcohol), a poly(vinyl butyral), a poly(methyl methacrylate), a polyacrylonitrile, a poly(vinylidene chloride), and a polysulfone. However, the shell-forming material is not limited to these mentioned above, and for example, a thermal melting material or a material to be destroyed by thermal expansion may also be used in the present invention.

When recycling of the scintillator and/or the image pickup element is taken into consideration, there may be preferably used an adhesive mixed with heat-expandable microspheres containing a foaming agent which generates a small amount of residue after peeling.

Since the image pickup element 4 must sense light emitted from the scintillator 6, the heat peelable adhesive 5 has optical transmission properties. Furthermore, the heat peelable adhesive 5 preferably has high transmittance in the visible light range. When the light emitted from the scintillator 6 is visible light, the heat peelable adhesive 5 is required to have a high transmittance of visible light. Hence, in particular, the transmittance is preferably 90% or more at the maximum luminous wavelength of the scintillator layer 8. In addition, since the resolution is decreased as the thickness of the heat peelable adhesive 5 is increased, the thickness thereof is preferably 200 μm or less and more preferably 50 μm or less. However, since the adhesive strength is also required, the thickness of the heat peelable adhesive 5 is preferably in a range of 1 to 50 μm.

Figure 3A:
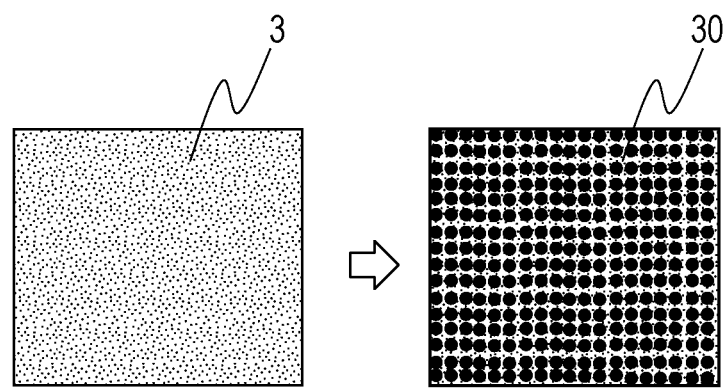
FIGS. 3A and 3B are schematic views each showing the reaction/change of decrease in adhesive strength of the reaction-induced phase separation material.
Figure 3B:
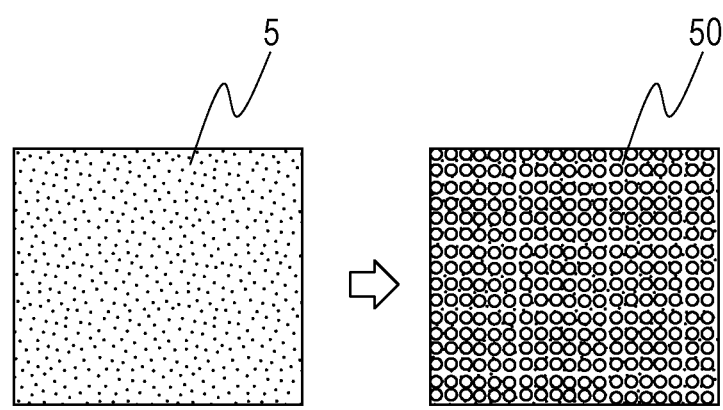

FIGS. 3A and 3B are schematic views showing the reaction/change of decrease in adhesive strength of the ultraviolet peelable adhesive 3 and that of the heat peelable adhesive 5, respectively. FIG. 3A shows the reaction/change before and after UV irradiation of the ultraviolet peelable adhesive 3 which performs a curing reaction by ultraviolet rays. Compared to the surface of the ultraviolet peelable adhesive 3 before curing (before UV irradiation) shown at the left side of FIG. 3A, many island-shaped aggregates are generated after curing (after UV irradiation) as shown at the right side of FIG. 3A, and as a result, an ultraviolet peelable adhesive 30 having a decreased adhesive strength is formed. FIG. 3B shows the reaction/change before and after a resin including heat-expandable microspheres, which is used as the heat peelable adhesive 5 in which its adhesive strength is decreased by heating, is heated. Compared to the surface of the heat peelable adhesive 5 before heating shown at the left side of FIG. 3B, many large island-shaped particles are generated after heating as shown at the right side of FIG. 3B, and as a result, a heat peelable adhesive 50 having a decreased adhesive strength is formed.

[Method for Manufacturing Radiation Image Pickup Apparatus]

Next, a method for manufacturing the radiation image pickup apparatus 1 will be described with reference to schematic cross-sectional views of FIGS. 4A to 4F each illustrating an exemplary manufacturing step.

First, the image pickup elements 4 each connected to the wiring board 10 are prepared, and the base 2 is prepared (not shown). Preparing may include positioning the image pickup elements 4 on the base 2 and connecting the wiring board 10 to each of the image pickup elements 4. In addition, preparing may include ensuring that contact surfaces of the base 2 and the image pickup elements 4 are clear of contaminants or dust.

Figure 4A:
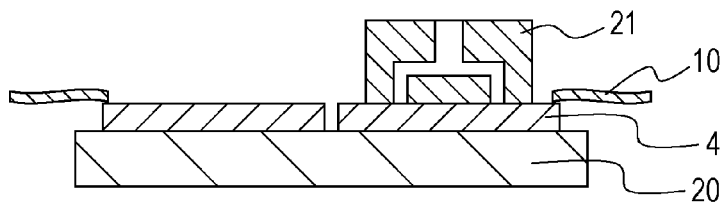
FIGS. 4A to 4F are cross-sectional views each illustrating a method for manufacturing the radiation image pickup apparatus according to Embodiment 1.

FIG. 4A shows the image pickup element 4 arranged on a stage 20 being picked up by a conveying device 21. The stage 20 fixes the image pickup elements 4 by suction so as not to disturb the arrangement of each image pickup element 4. Once the image pickup element 4 is fixed, the conveying device 21 grabs (by suction) the image pickup element 4 and lifts it, so that the base 2 may be positioned.

Figure 4B:
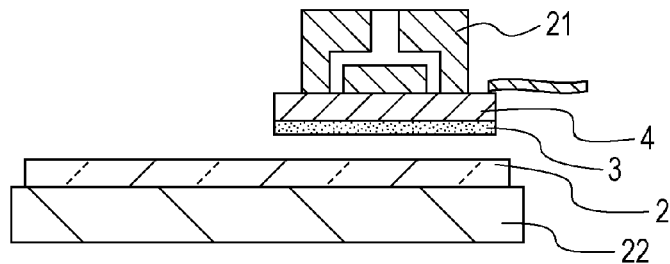

FIG. 4B shows a fixing step of adhering the image pickup element 4 on the base 2 fixed on a stage 22 with the ultraviolet peelable adhesive 3 used as a fixing member. The ultraviolet peelable adhesive 3 used as a fixing member is a material which decreases its adhesive strength by UV irradiation. After the separators 31 and 32 shown in FIG. 2A are peeled off, the ultraviolet peelable adhesive 3 is fixed to the image pickup element 4. Although the ultraviolet peelable adhesive 3 used as a fixing member is arranged at the image pickup element 4 side in FIG. 4B, it may be arranged at the base 2 side. In addition, the "fixing" in this specification indicates, besides the structure in which only the ultraviolet peelable adhesive 3 is arranged between the base 2 and the image pickup element 4, the structure in which at least one another material is arranged therebetween.

Figure 4C:
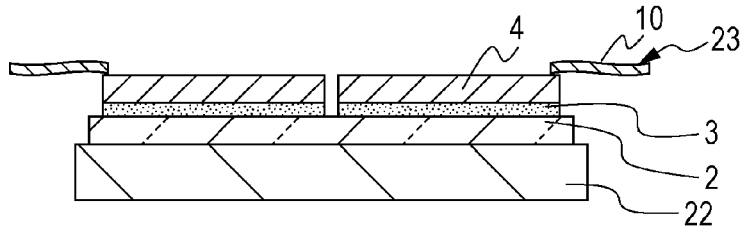

FIG. 4C shows a first inspection step of inspecting the image pickup elements 4. The inspection step is performed after the above fixing step is repeated predetermined times to arrange all of the image pickup elements 4 on the base 2 with the ultraviolet peelable adhesive 3. The inspection is performed such that the image pickup element 4 is irradiated with visible light, and a signal is read by a probe 23. When abnormality is discovered in the image pickup elements 4 in this step, an image pickup element having a defect is exchanged by irradiating the ultraviolet peelable adhesive 3 with ultraviolet rays. "The image pickup element having a defect" includes an image pickup element that exhibits an operation and/or an image outside the acceptable range due to generation of static electricity, involvement of foreign substances, and/or the like during mounting. The "repair" includes a work required to exchange an image pickup element having a defect and is also called "rework".

Figure 4D:
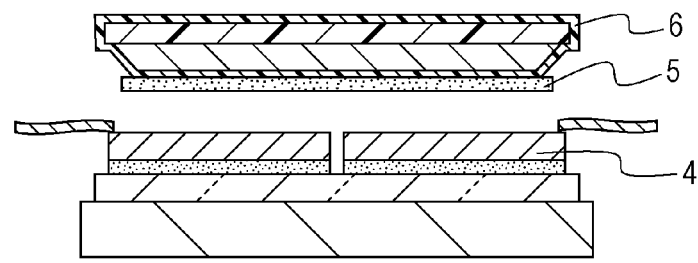

FIG. 4D shows a fixing step of adhering the scintillator 6 with the heat peelable adhesive 5 to be used as a fixing member. After the separators 51 and 52 shown with FIG. 2B are peeled off, the heat peelable adhesive 5 is fixed to the scintillator 6. Although the heat peelable adhesive 5 used as a fixing member is arranged at the scintillator 6 side in FIG. 4D, it may be arranged at the image pickup element 4 side.

Figure 4E:
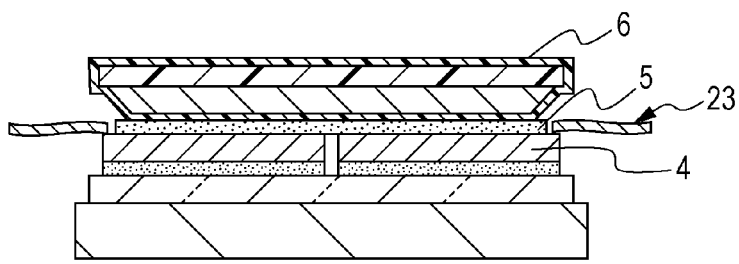
Figure 5A:
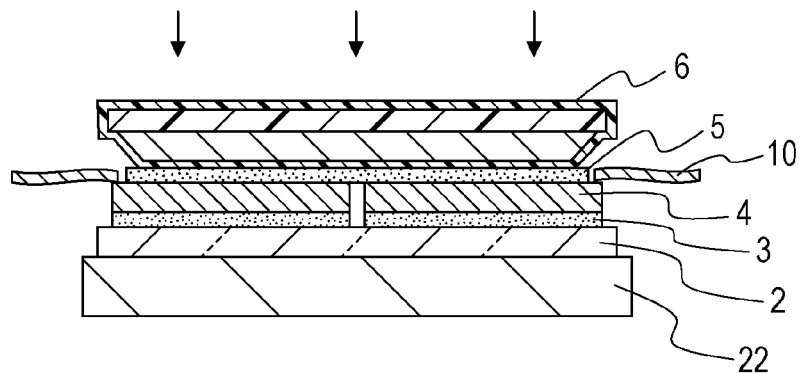
FIGS. 5A to 5C are cross-sectional views each illustrating a method for manufacturing the radiation image pickup apparatus according to Embodiment 1.
Figure 5B:
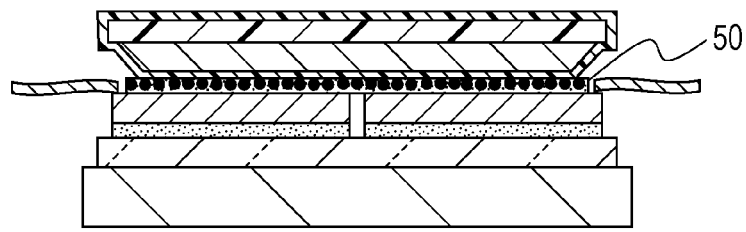
Figure 5C:
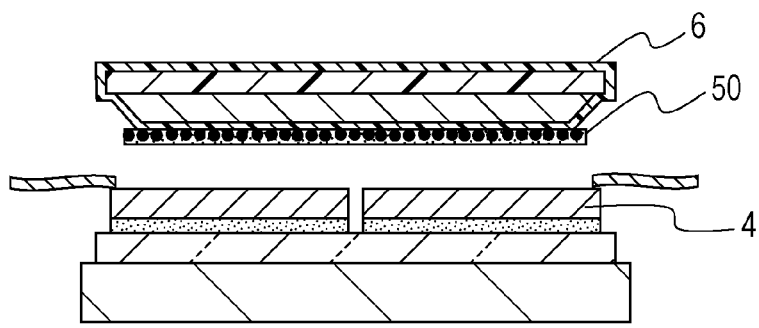
Figure 6A:
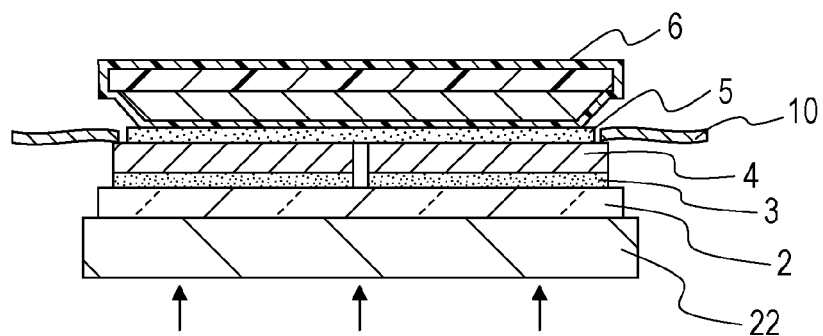
FIGS. 6A to 6C are cross-sectional views each illustrating a method for manufacturing the radiation image pickup apparatus according to Embodiment 1.
Figure 6B:
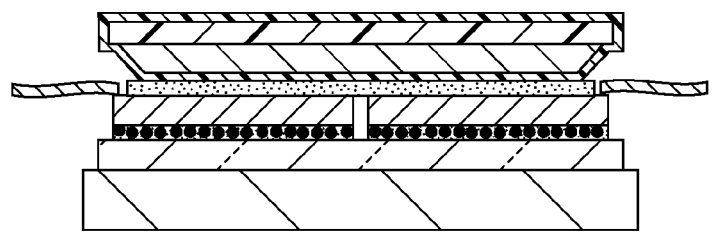
Figure 6C:
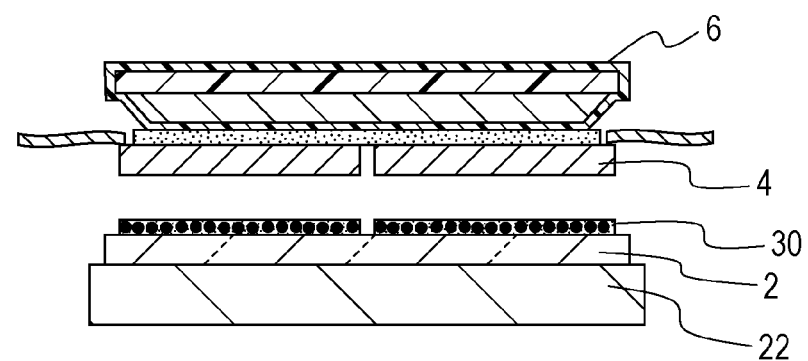

FIG. 4E shows a second inspection step of the image pickup elements 4 performed after the base 2, the image pickup elements 4, and the scintillator 6 are fixed. The inspection is performed such that the scintillator 6 is irradiated with radiation rays, and a signal is read by the probe 23. At this stage, the image pickup elements are each checked whether having a defect or not, and when judged as a defective product, this image pickup element is exchanged. Furthermore, the scintillator 6 is also inspected. When it is judged that the image is adversely affected due to defects of the scintillator 6, the scintillator 6 is exchanged. Feeling of the image pickup elements 4 and the scintillator 6 will be described with reference to FIGS. 5A to 6C. FIGS. 5A to 5C are each a cross-sectional view showing a heat separation step of separating the scintillator 6 and the image pickup elements 4. FIG. 5A shows the state in which a radiation image pickup apparatus having a laminated structure is heated which includes the base 2, the ultraviolet peelable adhesives 3, the image pickup elements 4, the heat peelable adhesive 5, and the scintillator 6 on the stage 22 in this order. In addition, as shown in FIG. 5B, the heat peelable adhesive 5 is changed by heating into the heat peelable adhesive 50 having a decreased adhesive strength. As a result, as shown in FIG. 5C, the scintillator 6 can be easily removed from the image pickup elements 4. At this stage, since fixed by the ultraviolet peelable adhesives 3, the image pickup elements 4 are each placed in a safe state. FIGS. 6A to 6C are each a cross-sectional view showing an UV irradiation separation step for separating the image pickup elements 4 and the base 2. FIG. 6A shows the state in which a radiation image pickup apparatus having a laminated structure which includes the base 2, the ultraviolet peelable adhesives 3, the image pickup elements 4, the heat peelable adhesive 5, and the scintillator 6 on the stage 22 in this order is irradiated with ultraviolet rays from the stage 22 side. In addition, as shown in FIG. 6B, the ultraviolet peelable adhesive 3 is changed by UV irradiation into the ultraviolet peelable adhesive 30 having a decreased adhesive strength. As a result, as shown in FIG. 6C, the image pickup elements 4 can be easily removed from the base 2. At this stage, since fixed by the heat peelable adhesive 5, the image pickup elements 4 are each placed in a safe state. In the case in which the image pickup elements 4 are removed from the base 2 in the state shown in FIG. 5C, when the surfaces of the image pickup elements 4 opposite to the base 2 are fixed by a conveyance means and are then irradiated with ultraviolet rays, at least one desired image pickup element 4 can be safely removed. For safe removal of the image pickup elements, the UV irradiation separation step of separating the base and the image pickup elements by irradiating the ultraviolet peelable adhesives with ultraviolet rays or the heat separation step of separating the image pickup elements and the scintillator by heating the heat peelable adhesive to decrease its adhesive strength is first performed. For safer removal of the image pickup elements, it is preferable that after the heat separation step is performed, the UV irradiation separation step be performed such that ultraviolet irradiation is performed while the image pickup elements are fixed, and the image pickup elements are then separated. In addition, as shown in the figure, when the ultraviolet peelable adhesives 3 are separated for the individual image pickup elements, only an image pickup element 4 to be exchanged can be easily removed. In this case, since an image pickup element 4 having no defect can be effectively used, cost can be reduced.

Figure 4F:
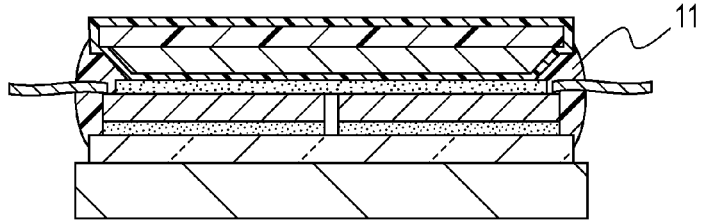

FIG. 4F shows a sealing step of sealing the periphery of a radiation image pickup apparatus having no defect, which is confirmed by the above inspection step, with the resin 11. The image pickup elements 4 are sealed by this step. Since fixed by the resin 11 in the sealing step, the wiring boards 10 penetrate the resin 11. The strength can be improved so that the base 2 and the scintillator 6 are not easily separated from each other, and the reliability can be improved by suppressing the entry of moisture and the like from the outside.

As described above, a radiation image pickup apparatus in which one or more image pickup elements are easily exchanged can be obtained. In addition, since the amount of residue of the fixing member is small on the surface of the base from which the image pickup element is removed, a next image pickup element can be easily fixed on the above surface.

In addition, when recycling is performed after the radiation image pickup apparatus is used as a product, the present invention can also be applied. In particular, every image pickup element of the radiation image pickup apparatus shown in FIGS. 1A and 1B is inspected, the resin 11 is removed, and one or more image pickup elements having a defect, which are confirmed by the steps shown FIGS. 5A to 6C, are exchanged, so that a new radiation image pickup apparatus can be manufactured.

Embodiment 2

Figure 7:
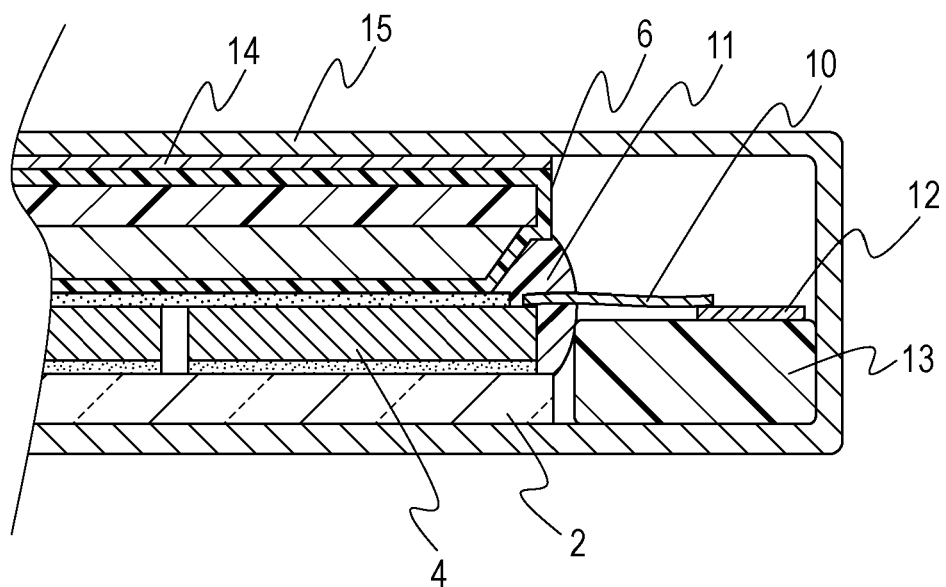
FIG. 7 is a partial cross-sectional view of a radiation image pickup apparatus according to Embodiment 2.

FIG. 7 is a partial cross-sectional view of a radiation image pickup apparatus according to Embodiment 2. In the radiation image pickup apparatus shown in FIG. 7, the same elements as those of the radiation image pickup apparatus shown in FIGS. 1A and 1B are designated by the same reference numerals as those described above, and detailed description thereof will be omitted. In the present embodiment, the apparatus described in Embodiment 1 is placed inside a external housing 15. Image pickup elements 4 are each a CMOS sensor formed on a silicon substrate. A wiring board 10 is a FPC. A base 2 is a glass sheet which transmits ultraviolet rays. A scintillator 6 has CsI:Tl as a scintillator layer. In addition, in the housing 15, the base 2, the image pickup elements 4, and the scintillator 6 are arranged, and a buffer material 14 is arranged between the scintillator 6 and the housing 15. A circuit element 12 which transfers and processes a signal is arranged for the image pickup element 4 through the wiring board 10. In addition, a buffer material 13 is arranged at side surfaces of a resin 11. The resin 11 and the buffer material 13 are preferably formed of a black resin which absorbs the wavelength of light to be sensed by the image pickup element 4. In addition, the buffer material 13 preferably surrounds all the peripheries of the resin 11. By virtue of the structure described above, light from a light emitting element of a different circuit board can be prevented from entering the image pickup element 4 through the base 2 or the like as stray light, and the image quality can be suppressed from being degraded.

Embodiment 3

Figure 8:
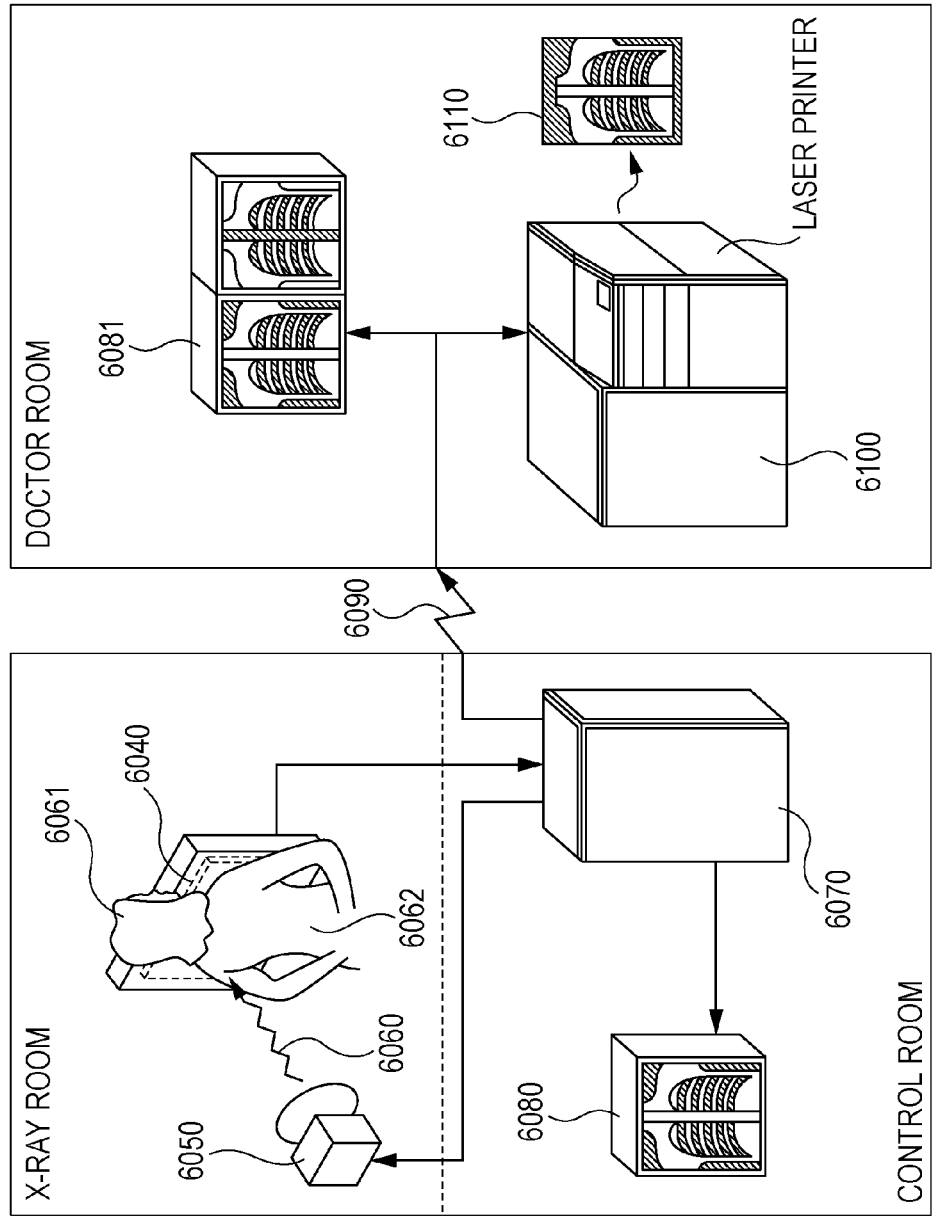
FIG. 8 is a schematic view illustrating a radiation image pickup system according to Embodiment 3.

FIG. 8 is a schematic view showing one application example of an x-ray radiation image pickup apparatus according to the present invention applied to an X-ray diagnostic system (radiation image pickup system). X-rays 6060 generated by an X-ray tube 6050 (radiation source) transmit a chest portion 6062 of a patient or a subject 6061 and are incident on an image sensor 6040 (radiation image pickup apparatus) including a scintillator mounted at an upper side. The information inside the body of the patient 6061 is included in the incident X-rays. Corresponding to the incidence of X-rays, the scintillator emits light, and this light is photoelectrically converted, so that electrical information is obtained. This information is converted into a digital signal, is processed by image processing using an image processor 6070, which is a signal processing device, and is then observed on a display 6080, which is a display device in a control room. In addition, the radiation image pickup system includes at least the radiation image pickup apparatus and the signal processing device which processes a signal from the radiation image pickup apparatus.

In addition, this information can be transferred to a remote location by a transmission processing device, such as a communications network 6090, and can be displayed on a display 6081 functioning as a display device in a doctor room at a different location or can be stored in a recording device, such as an optical disc, and a doctor at the remote location is able to diagnose the information. In addition, the information can be recorded on a film 6110 functioning as a recording medium by a film processor 6100 functioning as a recording device. Furthermore, the information can also be printed on paper by a laser printer functioning as a recording device.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-142951 filed Jun. 23, 2010, which is hereby incorporated by reference herein in its entirety.

What is claimed is:

1. A radiation image pickup apparatus comprising:
    a base which transmits ultraviolet rays;
    a plurality of image pickup elements each including a plurality of pixels, each of the pixels including a sensor portion for converting light into an image signal;
    a scintillator arranged on the image pickup elements at a side opposite to the base;
    an ultraviolet peelable adhesive, which reacts with incident ultraviolet light to decrease its adhesive strength, arranged between the base and the image pickup elements so as to fix the base and the image pickup elements in a predetermined position with respect to each other; and
    a heat peelable adhesive, which reacts with heat at a predetermined temperature or more to decrease its adhesive strength, arranged between the image pickup elements and the scintillator and which fixes the image pickup elements to the scintillator.

2. The radiation image pickup apparatus according to claim 1, wherein the heat peelable adhesive is an adhesive mixed with heat-expandable microspheres containing a foaming agent.

3. The radiation image pickup apparatus according to claim 1, further comprising a resin arranged between the base and the scintillator to surround the peripheries of the image pickup elements.

4. The radiation image pickup apparatus according to claim 3, further comprising wiring boards which penetrate the resin and which are connected to the image pickup elements.

5. The radiation image pickup apparatus according to claim 1,
    wherein each of the plurality of image pickup elements is fixed to the base with one of the ultraviolet peelable adhesive, such that a plurality of ultraviolet peelable adhesives is arranged on the base in correspondence with the plurality of image pickup elements, and
    wherein the ultraviolet peelable adhesives are separated from each other.

6. The radiation image pickup apparatus according to claim 1, wherein the heat peelable adhesive has optical transmission properties which transmit light from the scintillator and has a thickness of 1 to 50 μm.

7. A radiation image pickup system comprising:
    the radiation image pickup apparatus according to claim 1; and
    a signal processing device configured to process the image signal.

8. A method for manufacturing a radiation image pickup apparatus, comprising the steps of:
    preparing a base which transmits ultraviolet rays;
    preparing a plurality of image pickup elements each including a plurality of pixels, each pixel including a sensor portion for converting light into an image signal;
    preparing a scintillator;
    disposing an ultraviolet peelable adhesive, which reacts with incident ultraviolet rays to decrease its adhesive strength, between the base and the image pickup elements so as to fix the base and the image pickup elements in a predetermined position with respect to each other; and
    fixing the scintillator on the image pickup elements at a side opposite to the base with a heat peelable adhesive provided therebetween, wherein the heat peelable adhesive reacts with heat at a predetermined temperature or more to decrease its adhesive strength.

9. The method for manufacturing a radiation image pickup apparatus according to claim 8, further comprising the step of:
   inspecting the image pickup elements fixed to the base; and
   when at least one image pickup element is judged as a defective image pickup element in the inspecting step, performing at least one of a first separation step of separating the defective image pickup element from the base by irradiating the ultraviolet peelable adhesive with ultraviolet rays to decrease the adhesive strength thereof and a second separation step of separating the defective image pickup element from the scintillator by heating the heat peelable adhesive to decrease the adhesive strength thereof.

10. The method for manufacturing a radiation image pickup apparatus according to claim 9,
    wherein, after the second separation step is performed by heating, the step of disposing the ultraviolet peelable adhesive between the base and the image pickup elements is repeated so that the ultraviolet peelable adhesive is irradiated with ultraviolet rays while the image pickup elements are fixed.

11. A radiation image pickup apparatus comprising:
    a base which transmits ultraviolet rays;
    a plurality of image pickup elements each including a plurality of pixels, each of the pixels including a sensor portion for converting light into an image signal; and
    a plurality of ultraviolet peelable adhesives, each of which reacts with incident ultraviolet light to decrease its adhesive strength, arranged between the base and the plurality of image pickup elements so as to fix the base and the plurality of image pickup elements in a predetermined position with respect to each other,
    wherein the plurality of ultraviolet peelable adhesives is separated from each other, and the plurality of ultraviolet peelable adhesives is arranged on the base in correspondence with the plurality of image pickup elements.

12. The radiation image pickup apparatus according to claim 11, further comprising;
    a scintillator arranged on the image pickup elements at a side opposite to the base;
    a heat peelable adhesive, which reacts with heat at a predetermined temperature or more to decrease its adhesive strength, arranged between the image pickup elements and the scintillator and which fixes the image pickup elements to the scintillator; and
    a resin arranged between the base and the scintillator to surround the peripheries of the image pickup elements.

13. The radiation image pickup apparatus according to claim 12, further comprising wiring boards which penetrate the resin and which are connected to the image pickup elements.

14. A radiation image pickup system comprising:
    the radiation image pickup apparatus according to claim 11; and
    a signal processing device configured to process the image signal.

15. A radiation image pickup apparatus comprising:
    a plurality of image pickup elements each including a plurality of pixels, each of the pixels including a sensor portion for converting light into an image signal;
    a scintillator arranged on the image pickup elements; and
    a heat peelable adhesive, which reacts with heat at a predetermined temperature or more to decrease its adhesive strength, arranged between the plurality of image pickup elements and the scintillator and which fixes the plurality of image pickup elements to the scintillator.

16. The radiation image pickup apparatus according to claim 15, wherein the heat peelable adhesive is an adhesive mixed with heat-expandable microspheres containing a foaming agent.

17. The radiation image pickup apparatus according to claim 16, further comprising;
    a base which transmits ultraviolet rays;
    a plurality of ultraviolet peelable adhesives, each of which reacts with incident ultraviolet light to decrease its adhesive strength, arranged between the base and the plurality of image pickup elements so as to fix the base and the plurality of image pickup elements in a predetermined position with respect to each other; and
    a resin arranged between the base and the scintillator to surround the peripheries of the image pickup elements.

18. The radiation image pickup apparatus according to claim 17, further comprising wiring boards which penetrate the resin and which are connected to the image pickup elements.

19. The radiation image pickup apparatus according to claim 15, wherein the heat peelable adhesive has optical transmission properties which transmit light from the scintillator and has a thickness of 1 to 50 μm.

20. A radiation image pickup system comprising:
    the radiation image pickup apparatus according to claim 15; and
    a signal processing device configured to process the image signal.

* * * * *